(12) United States Patent
Yrjänheikki et al.

(10) Patent No.: US 6,277,393 B1
(45) Date of Patent: Aug. 21, 2001

(54) SYSTEMIC AND/OR LOCAL (TOPICAL) APPLICATION OF TETRACYCLINE AND/OR TETRACYCLINE DERIVATIVE(S) FOR TREATING, SUPPRESSING AND PREVENTING OF CEREBROVASCULAR DISEASES, TRAUMAS AND DAMAGES OF NERVOUS SYSTEM

(75) Inventors: Juha Yrjänheikki, Ylitornio; Pertti Törmälä, Tampere; Riitta Keinänen, Kuopio; Nina Vartiainen, Jämsä; Susanna Miettinen, Kuopio; Auvo Kaikkonen, Tampere; Jari Koistinaho, Vuorela, all of (FI)

(73) Assignee: Bioabsorbable Concepts, Inc., Tampere (FI)

(*) Notice: Subject to any disclaimer, the term of this patent is extended or adjusted under 35 U.S.C. 154(b) by 0 days.

(21) Appl. No.: 09/522,855

(22) Filed: Dec. 10, 1999

Related U.S. Application Data

(63) Continuation of application No. 09/000,914, filed on Dec. 30, 1997, now abandoned.

(51) Int. Cl.[7] .............. A61F 2/00; A01N 25/34; A61K 9/14

(52) U.S. Cl. ............ 424/426; 424/489; 424/408

(58) Field of Search .................. 424/426, 427, 424/489, 408; 604/89.1; 264/4.3

(56) References Cited

U.S. PATENT DOCUMENTS

| | | | |
|---|---|---|---|
| 5,143,661 | * | 9/1992 | Lawter et al. .............. 264/4.3 |
| 5,290,271 | * | 3/1994 | Jernberg ................ 604/89.1 |
| 5,308,624 | * | 5/1994 | Maincent et al. ............ 424/427 |

OTHER PUBLICATIONS

Clark et al. "Doxycycline Treatment Reduces Ischemic Brain Damage in Transient Middle Cerebral Artery Occlusion in the Rat" J. Molecular Neuroscience (1997) 9:103–108.*

Weingart et al. "The role of minocycline in the treatment of intracrnial 9L glioma" J.Neurosurg. (1995) 82:635–640.*

Clark et al. "Reduction of Central Nervous System Reperfusion Injury in Rabbits Using Doxycycline Treatment" Stroke (1994) 25(7):1411–1416.*

Gert J. Ter Horst, Jakob Korf, Stroke: Prevalence and Cell Death, Clinal Pharmacology of Cerebral Ischemia, 1997, pp. 1–30.

Keith W. Muir, MRCP; Kennedy R. Lees, FRCP, Clinical Experience With Excitatory Amino Acid antagonist Drug, Stroke vol. 26, No. 3, 1995, pp. 503–513.

Johannes Kornhuber and M. Weller, Biol Psychiatry, 1997; 41:135–144, Psychotogenicity and N–methyl–D–aspartate Receptor Antagonism: Implications for Neuroprotective Pharmacotherapy.

Buchan et al., Supplement I Stroke, vol. 24, No. 12, Dec. 1993, 148–154, AMPA Antagonists: Do They Hold More Promise for clinical Stroke Trials Than NMDA Antagonists?.

(List continued on next page.)

*Primary Examiner*—Thurman K. Page
*Assistant Examiner*—Blessing Fubara
(74) *Attorney, Agent, or Firm*—Kenyon & Kenyon

(57) ABSTRACT

A method for treating and/or preventing of cerebrovascular diseases, traumas and damages of the nervous system, which method includes local (topical) and/or systemic application of an effective amount of tetracycline and/or tetracycline derivative or a mixture of tetracycline and/or tetracycline derivative(s) ("active agent(s)"), optionally in a pharmaceutically-acceptable diluent, carrier or release system ("active compostition").

7 Claims, 5 Drawing Sheets

*protection significant, p< 0.001, Student's T test

OTHER PUBLICATIONS

Liu et al, Department of Neurology, Medical University of South Carolina, 1989, 589–593, Polyethylene glycol–conjugated superoxide dismutase and catalase reduce ischemic brain injury.

Chan et al., Annals of Neurology vol. 21, No. 6, Jun. 1987, 540–547, Protective Effects of Liposome–Entrapped Superoxide Dismutase on Posttraumatic Brain Edema.

Paul A. Insel, Analgesic–Antipyretics and Antiinflammatory Agents, Ch. 26, pp. 638–681, Analgesic–Antipyretics and Antiinflammatory Agents: Drugs Employed In the Treatment of Rheumatoid Arthritis and Gout.

Grilli et al., Science, vol. 274, Nov. 1996, 1383–1385, Neuroprotection by Aspririn and Sodium Salicylate Through Blockade of NF–kB Activation.

Andres Goth, M.D., Medical Pharmacology, Principals and Concepts, Sixth Edition, 1972, 555–556, Antibiotic Drugs Amin et al., FEBS Letters 410 (1997) 259–264, Post–transcriptional regulation of inducible nitric oxide synthase mRNA in murine macrophages by doxycycline and chemically modified tetracyclines.

Basic and Clinical Pharmacology, Bertram G. Katzung (Ed.), 4th Edition, Ch. 44, 567–570, Chloramphenicol & Tetracyclines.

Zhang et al. Journal of Cerebral Blood Flow and Metabolism, vol. 17, No. 2, 123–135, 1997, A New Rat Model of Thrombotic Focal Cerebral Ischemia.

Muir KW et al. "Clinical Pharmacology of CNS 1102 in Volunteers" Ann. NY Acad. Sci. (1995) 765: 279–289.

Marshall LF et al. "Pharmacologic Therapy: Promising Clinical Investigations" New Horiz. (1995) 3:573–80.

Bullock R "Strategies for Neuroprotection with Glutamate Antagonists" Ann. NY Acad. Sci (1995) 765: 272–278.

Olney JW (1994) "Neurotoxicity of NMDA Receptor Antagonists: An Overview" Psychopharmacol. Bull. (1994) 30:533–540.

Swanson RA, et al. "A Semiautomated Method for Measuring Brain Infarct Volume" J. Cereb. Blood Flow Metab. (1990) 10:290–296.

E.A. Neuwelt et al. "Therapeutic Efficacy of Multiagent Chemotherapy with Drug Delivery Enhancement by Blood–Brain Barrier Modification in Gliobastoma" Neurosurgery 19 (1986) 579–582.

M.K. Gumerlock et al. "Osmotic blood–brain barrier disruption and chemotherapy in the treatment of high grade malignant glioma: patient series and literature review" J. Neuroooncol., 12 (1992) 33–46.

Clark et al, "Doxycycline Treatment Reduces Ischemic brain Damage in Transient Middle Cerebral Artery Occlusion in the Rat," Journal of Molecular Neuroscience (Oct. 9, 1997), (2): 103–8.

Weingart J.D. et al. "The Role of Minocycline in teh Treatment of Intracranial 9L glioma" J. Neurosurg. (Apr. 1995) vol. 82, 635–640.

Dienel et al. "Uptake of Radiolabeled ions in normal and ischemia–damaged brain," Ann. of Neurology, Abstract (1986) vol. 19, No. 5, pp. 465–472.

Clark et al. "Reduction of central nervous system reperfusion injury in rabbits using doxycycline treatment" Stroke, Abstract (1994), vol. 25, No. 7, pp. 1411–1416.

Webber, W. et al., "Characterization of soluble, salt–loaded degradable PLGA films and their release of tetracycline," J. of Biomed. Matl. Research, Abstract (Jul. 1998), vol. 41, No. 1, pp. 18–29.

Stoller et al., J. of Periodontology, Abstract, (Oct. 1998), vol. 69, No. 10, 1085–1091.

Copies of Written Opinion and International Search Report for PCT/US98/27294 (PCT publication WO 99/33455), the PCT appliction that corresponds to this application Ser. No. 09/522,855.

* cited by examiner

| | $R_7$ | $R_6$ | $R_5$ | Renal Clearance (mL/min) |
|---|---|---|---|---|
| Chlortetracycline | −Cl | −CH₃ | −H | 35 |
| Oxytetracycline | −H | −CH₃ | −OH | 90 |
| Tetracycline | −H | −CH₃ | −H | 65 |
| Demeclocycline | −Cl | −H | −H | 35 |
| Methacycline | −H | =CH₂ * | −OH | 31 |
| Doxycycline | −H | −CH₃ * | −OH | 16 |
| Minocycline | −N(CH₃)₂ | −H | −H | 10 |

*there is no -OH at position 5 on methacycline and doxycycline

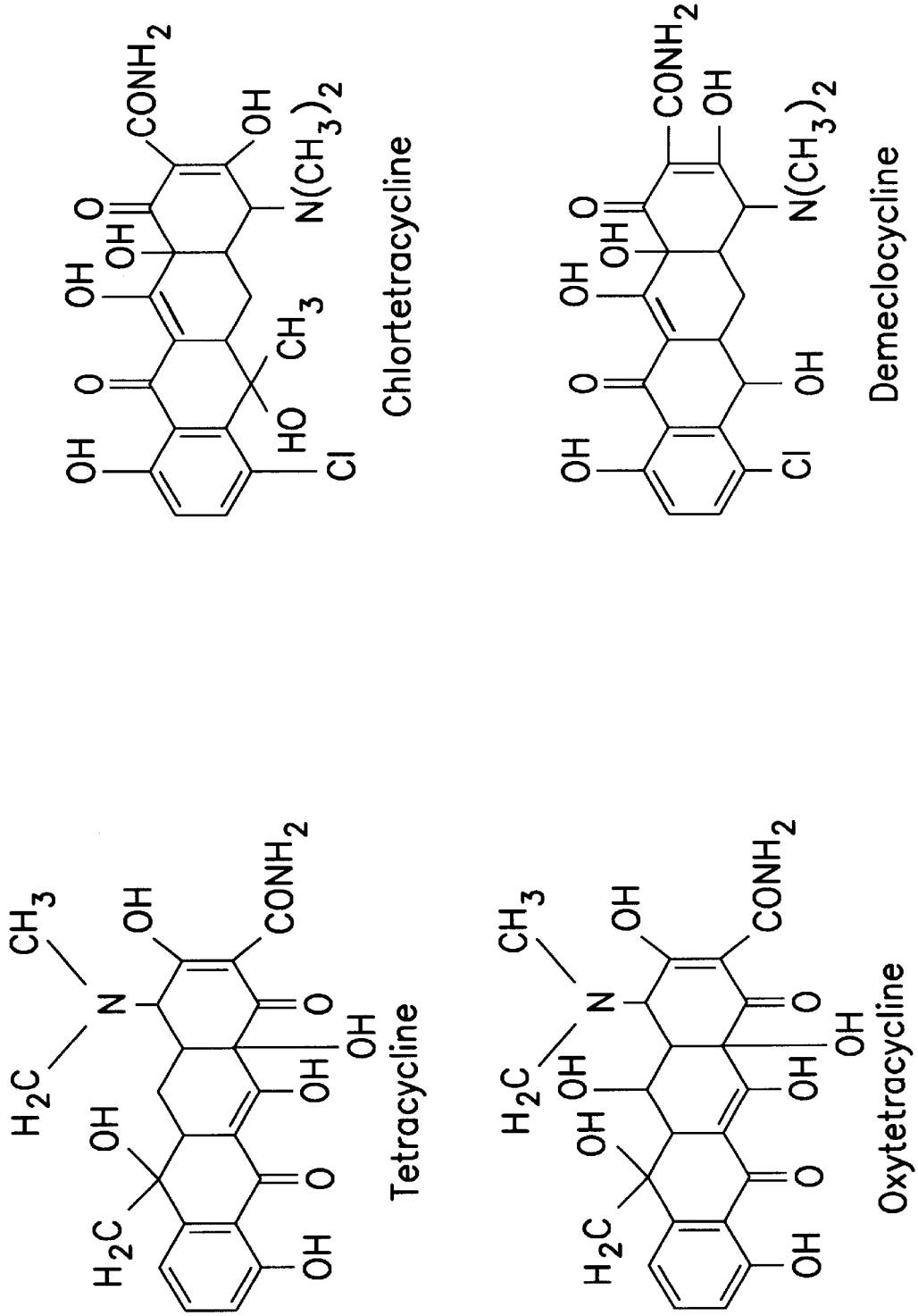
Fig. 1B.1

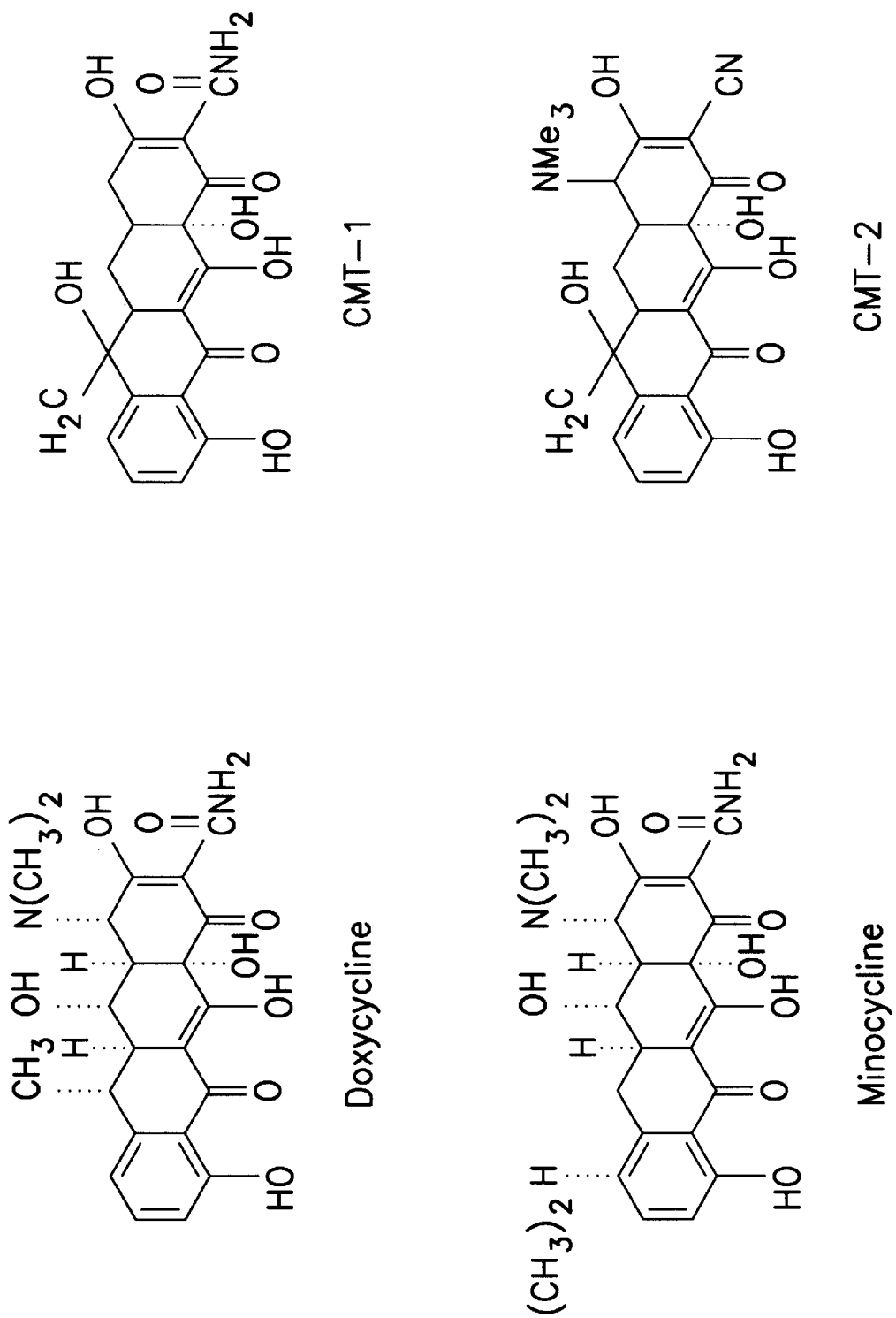
Fig. 1B.2

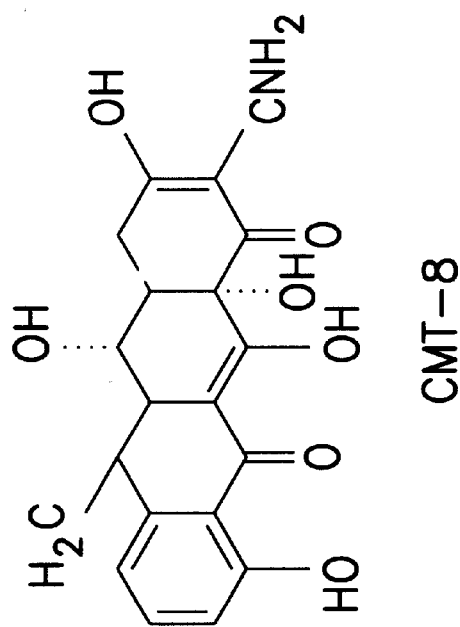
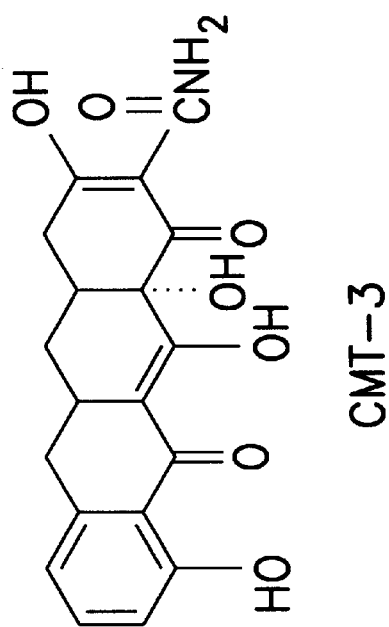
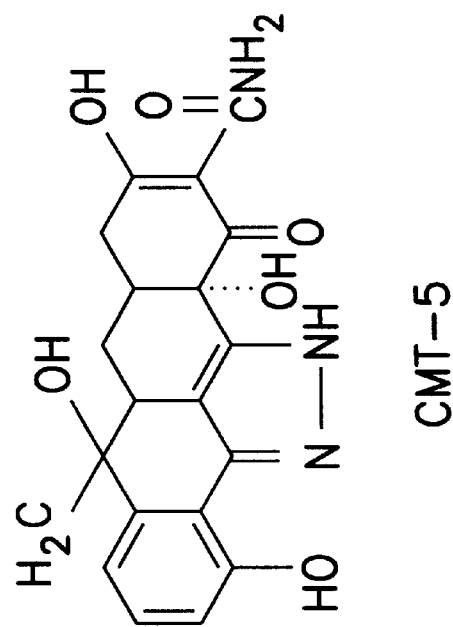
Fig. 1B.3

SYSTEMIC AND/OR LOCAL (TOPICAL) APPLICATION OF TETRACYCLINE AND/OR TETRACYCLINE DERIVATIVE(S) FOR TREATING, SUPPRESSING AND PREVENTING OF CEREBROVASCULAR DISEASES, TRAUMAS AND DAMAGES OF NERVOUS SYSTEM

This application is a continuation of application Ser. No. 09/000,914, filed Dec. 30, 1997, now abandoned.

FIELD OF THE INVENTION

This invention is in the area of the treatment and/or preventing of cerebrovascular diseases, traumas and damages of the nervous system ("neural injuries"), and includes local (topical) or systemic application of an effective amount of tetracycline, tetracycline derivative or a mixture of tetracycline and/or tetracycline derivative(s) ("active agent(s)"), optionally in a pharmaceutically-acceptable diluent, carrier or tetracycline release system ("active composition").

BACKGROUND OF THE INVENTION

Degeneration, traumas and injuries of the nervous system, comprising brain, spinal cord and peripheral nerves, are characteristic of certain diseases and common consequences of accidents. Cerebrovascular accident (CVA) is a clinical definition used to describe symptoms of an acute neurological disorder caused by disturbance of the cerebral blood supply. Intracerebral and subarachnoid hemorrhages account for approx 20% of CVAs and 80% are of ischemic type. Stroke defines all conditions in which the duration of the CVA symptoms exceeds 24 h. Hemorrhagic strokes may be situated intra- or extracerebrally. Intracerebral hemorrhage can be caused by artery aneurysm rupture, and a subdural hemorrhage by cranial trauma. See, Ter Horst G J and Postigo A., In: Ter Horst G J and Korf J (eds.), ClinicalPharmacology of Cerebral Ischemia, Humana Press, Totowa, N.J., 1–30, 1997, the entire disclosure of which is incorporated herein by reference.

The causes of ischemic stroke are numerous and include large artery atherosclerosis, small vessel occlusion, embolisms, and thrombosis. Focal (regional) ischemia is clinically more common than global (forebrain) ischemia A focal insult usually occurs after thrombosis or embolus in the middle cerebral artery, whereas global ischemia results from transient cardiac arrest. See, Ter Horst G J and Postigo A., In: Ter Horst G J and Korf J (eds.), Clinical Pharmacology of Cerebral Ischemia, Humana Press, Totowa, N.J., 1–30, 1997.

If such damages, traumas or injuries as described above are not treated in a proper way they can lead to extensive death of nerve cells leading further to several permanent symptoms, including paralysis and other motor dysfunctions, sense disorders, mental disorders or even death of the patient.

The need to control cerebrovascular accidents and spinal cord injuries has led to a search for therapeutic agents and treatment methods that are both safe and effective. Animal studies and clinical trials have shown that amino acid transmitters (especially glutamate), oxidative stress and inflammatory reactions contribute strongly to cell death in brain diseases and damages. There are available some pharmacological methods to prevent cell deaths in the above cases. However, these methods have severe limitations and/or side-effects so that in practice there is no effective medical method for the treatment of cerebral stroke and spinal cord injuries. For example, MK-801 (5-methyl-10,11-dihydro-5H-dibenzo[a,d]cyclohepten-5,10-imine hydrogen maleate, dizocilpine maleate) and CNS 1102 block another type of glutamate receptor and are neuroprotective in several rodent models of brain ischemia. See, Muir K W, Grosset D G and Lees K R (1995). Ann. NY Acad. Sci. 765:279–289; Muir K W, Lees K R (1995). Stroke 26:503–513; Kornhuber J, Weller M (1997). Biol. Psych. 41:135–144; Marshall L F, Marshall S B (1995). New Horiz. 3:573–580; Bullock R (1995). Ann. NY Acad. Sci 765:272–278; the entire disclosures of which are each incorporated herein by way of this reference. However, these compounds lead to hallucinations and cause vacuolization and death of certain cortical neurons. See Olney J W (1994). Psychopharmacol. Bull. 30:533–540, the entire disclosure of which is incorporated herein by this reference. NBQX (6-nitro-7-sulphamoylbenzo (f) quinoxaline-2,3dione (disodium)) acts as an antagonist of glutamate receptors, but it causes interstitial tubular nephrite and hallusinations. See, Muir K W, Lees K R (1995). Stroke 26:503–513;Marshall L F, Marshall S B (1995). New Horiz. 3:573–580; and Buchan A M, Lesiuk H, Bames K A, Li H, Huang Z-G, Smith K E, Xue D (1993). Stroke 24:I148–I151, Suppl. I, the entire disclosures of which are incorporated herein by way of this reference. Oxidative stress can be prevented with antioxidative enzymes, which unfortunately have very short half-life, typically only minutes or hours, in vivo. e.g. Cu,Zn-superoxidedismutase (Cu, Zn-SOD) protects cells agains oxidative stress but its half-life in vivo is, in free form, 6 min and, as conjugated, 38 hours. See Liu T H, Beckman J S, Freeman B A, Hogan E L and Hsu Y (1989). Am. J. Physiol. 256:H589–H593, the entire disclosure of which is incorporated herein by this reference. In addition, even though antioxidative compounds and anti-inflammatory drugs cross the blood-brain barrier, cerebral concentration high enough for neuronal protection is not usually achieved. See Chan P H, Longar S, Fishman R A (1987). Ann. Neurol. 21:540–547.;Insel P A: Chapter 26, 638–681 in: Goodman and Gilman (eds) the Pharmacological Basis of Therapeutics. Eight edition, Pergamon Press, New York, 1990; and Grilli M, Pizzi M, Memo M, Spano P (1996). Science 274:1383–1385; the entire disclosures of which are incorporated herein by way of this reference.

As a result, there is a significant and very long-standing need to identify new methods and/or new agents with favourable benefit to risk ratios that can be applied topically (locally) or given systemically to prevent or suppress (i.e. "treat") neuronal death after damages, traumas and diseases of the brain and spinal cord, and the associated symptoms of paralysis, cardiac complications, psychosis and agitation. Optimally, such agents should be effective when administered topically (locally) or systemically and systemic absorption should not result in blood levels high enough to cause significant systemic toxicity or other adverse side effects.

It is therefore an object of the present invention to provide methods for treating brain stroke (brain ischemias and hemorrhages) and spinal cord injuries.

It is another object of the present invention to provide methods for systemic treatment of brain stroke (brain ischemias and hemorrhages) and spinal cord injuries.

It is yet another object of the present invention to provide methods for topical/local treatment of brain ischemias (brain stroke) and spinal cord injuries.

SUMMARY OF THE INVENTION

A method for treating brain stroke (ischemia, hemorrhage) and/or spinal cord injuries in a human or other mammal is disclosed that involves the administration of an effective amount of tetracycline and/or tetracycline derivative or a mixture of tetracycline and/or tetracycline derivatives ("active agent(s)"), optionally in a pharmacuitically-acceptable diluent, carrier or release matrix ("active composition"). The treatment can be used for brain stroke and/or spinal cord injury occuring in any area of the brain or spinal cord. Additionally, patients with brain stroke and/or spinal cord injuries may have a tendency to develop cerebral edema, cardiac complications, dysfunction of the autonomic nervous system, psychosis and agitation. These related conditions can also be prevented and/or treated with active agents(s) and/or active composition according to the method of the invention. In a preferred embodiment for the treatment of brain ischemia and/or spinal cord injury, active agent(s) and/or active composition is administered intravenously or intra-arterially and the administration is continued orally. In another preferred embodiment for the treatment of brain ischemia and/or spinal cord injury, active agent(s) and/or active composition is administered locally on or into brain or spinal cord by means of a diluent, a carrier or drug releasing system.

The active agent and/or active composition can be administered in any dosage that achieves the desired result. Systemic dosages of between 10 and 180 mg/kg/day are typically useful for the above indications. The dosages can be given at any appropriate interval, and typically in the beginning once a day, up to several times a day.

In the embodiment of the invention where tetracycline and/or tetracycline derivative, or a mixture of tetracycline and/or tetracycline derivatives, is administered locally (topically), the active agent can be administered in any appropriate topical composition, including in an ointment, gel, cream, lotion, suspension, spray, powder, paste, aerosol, microcapsules, hydrogels, short or long fibers or fiber constructions, like threads, cords, fabrics, meshes, nonwoven felts, laminates or membranes and polymeric films. The active agent can be administered topically to the brain or spinal cord tissue, for example, so that the composition consists of an inert bioabsorbable polymer, copolymer or polymer blend implant, in some form given above, which implant starts to release the active agent(s) immediately when it has been placed in contact with the surface and/or internal structure of the brain or spinal cord, and continues the release of the active agent(s) for days and weeks in a controlled manner.

After contact with the surface of the brain, the active agent(s) can diffuse into deeper structures of the brain. When implanted inside of brain tissue into the damaged area, the implant including active agent(s), release(s) the active agent (s) into the surrounding brain cells.

BRIEF DESCRIPTION OF THE DRAWINGS

FIGS. 1A and 1B describe the structural formulas of tetracycline and some tetracycline derivatives.

DETAILED DESCRIPTION OF THE INVENTION

Methods for treating, suppressing and preventing of cerebrovascular and neurodegenerative diseases, traumas and damages of brain and spinal cord are disclosed, which include administering an effective amount of tetracycline and/or tetracycline derivative or a mixture of tetracycline and/or tetracycline derivative(s), optionally in a pharmaceutically acceptable diluent, carrier or drug-release matrix for systemic or topical (local) application.

I. Tetracycline Derivatives

Figure 1A:
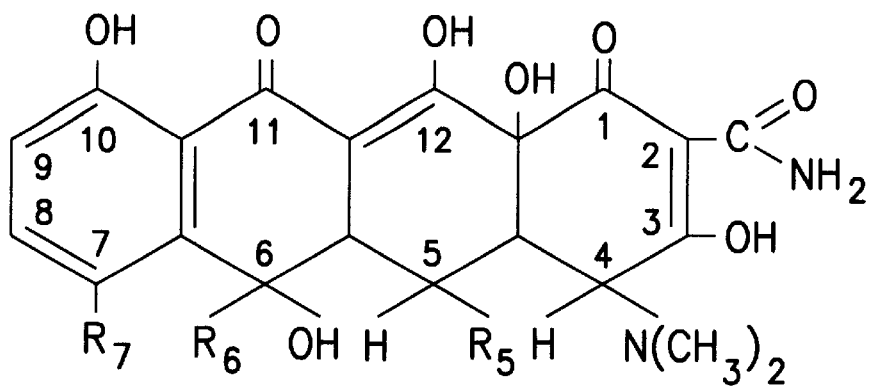

FIGS. 1A and 1B show the structural formulas of tetracycline and some tetracycline derivatives (CMT=chemically modified tetracyclines), which either alone or as mixtures are effective in the applications of the invention. See, A. Goth, Medical Pharmalogy, The C.V. Mosby Company, St. Louis, USA, 1972, pp. 555–556; A. R. Amin et al, FEBS Letters 410 (1997) 259–264; and Basic and Clinical Pharmacology, B G Katzung (ed.), 4th Edition, pp. 567–570; the entire disclosures of which are incorporated herein by way of this reference.

The hydrophobic (or hydrophilic) character of tetracycline derivatives can be varied by adding one or more lipophilic (or charged) side chains onto the molecule or by altering some existing functional group or side chain to make it less polar (or more polar). By adjusting the hydrophobicity of the molecule in a proper way, optimal penetration through blood-brain barrier (BBB) and/or release from the carrier or release matrix vecicle can be achieved. The BBB can be opened temporarily through the administration of intracarotic hyperosmolar mannitol. See, E. A. Neuwelt et al. Neurosurgery 19 (1986) 573–582; and M. K. Gumerlock et al. J. Neurooncol., 12 (1992) 33–46); the entire disclosures of which are incorporated herein by way of this reference. This method can be applied in conjunction with the active agent(s) and/or active compositions of the invention to enhance their penetration through BBB.

II. Therapeutic Compositions

A. Systemic Administration

In one embodiment of the invention, tetracycline and/or tetracycline derivative and/or tetracycline derivative mixture (active agent(s)) is administered systematically to treat brain stroke (ischemia/hemorrhage) and/or all of the other described conditions. The active agent(s) can be administered subcutaneously, intravenously, intraperitoneally, intramuscularly, parenterally, orally, submucosally, by inhalation, intranasally, transdermally via a slow release patch, or locally (topically), in an effective dosage range to cause retardation or prevention of the harmful effects of brain stroke and/or spinal cord injury.

Typical systemic dosages for all of the above-identified conditions are those ranging from between approximately 5 and 180 mg/kg per day, as a single daily dose or divided daily doses.

The active agent(s) is (are) administered for a sufficient time period to alleviate the undesired symptoms and the clinical signs, symptoms or pathologies associated with brain stroke and/or spinal cord injury.

The active agent(s) is (are) included in the pharmaceutically acceptable carrier, release matrix or diluent in an amount sufficient to deliver to a patient a therapeutic amount of compound of tetracycline and/or tetracycline derivative (s), in vivo, in the absence of serious toxic effects.

The concentration of active agent(s) in the drug composition will depend on absorption, inactivation, and excretion rates of the drug(s) as well as other factors known to those of skill in the art.

It is to be noted that dosage values will also vary with the severity of the condition to be alleviated. It is to be further understood that for any particular subject, specific dosage regimens should be adjusted over time according to the individual need and the professional judgement of the person administering or supervising the administration of the compositions, and that the dosage ranges set forth herein are exemplary only, and are not intended to limit the scope or practice of the claimed composition.

B. Oral Administration

Oral administration is a simple mode of systemic administration. Oral compositons will generally include an inert diluent or an edible carrier. They may be enclosed in gelatin capsules or compressed into tablets. For the purpose of oral therapeutic administration, the active agent(s) can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active agent(s) and/or composition(s) can be administered as a component of an elixir, suspension, syrup, wafer or the like. A syrup may contain, in addition to the active compounds, sucrose as a sweetening agent and certain preservatives, dyes and colorings and flavors.

C. Intravascular Administration

If administered intravascularly (e.g., intravenously or intra-arterially), preferred carriers are bacteriostatic water, physiological saline, Cremophor EL™ (BASF, Parsippany, N.J.) or phosphate buffered saline (PBS).

In one embodiment of the invention, the active agent(s) is (are) prepared with a carrier that will protect the active agent(s) against rapid elimination from the body, such as a controlled release matrix, including implants and microencapsulated delivery systems. Bioabsorbable, biocompatible polymers can be used, such as poly-$\alpha$-hydroxy acids (e.g. polylactides, polyglycolide and their copolymers), polyanhydrides, collagen, polyorthoesters, or tyrosine polycarbonates. Methods for preparation of active compositions of active agent(s) and of bioabsorbable polymer(s) will be apparent to those skilled in the art. Suitable bioabsorbable polymers to be used in manufacturing of such formulations are mentioned, e.g., in U.S. Pat. No. 4,968,317, U.S. Pat. No. 5,618,563, FI Patent No. 98136, and FI Patent No. 100217 B, the entire disclosures of which are incorporated herein by way of this reference.

Liposomal suspensions including, optionally, liposomes targeted to damaged cells (liposomes with functional groups with which the liposomes can recognize the damaged cells) are also preferred as pharmaceutically acceptable carriers. These may be prepared according to methods known to those skilled in the art, for example, as described in U.S. Pat. No. 4,522,811, which is incorporated herein by reference in its entirety. For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an organic solvent that is then evaporated, leaving behind a thin film of dried lipid on the surface of the container. An aqueous solution of active agent(s) is then introduced into the container. The container is then swirled by hand to free lipid material from the sides of the container and to disperse lipid aggregates, thereby forming the liposomal suspension.

D. Local (Topical) Administration

In another embodiment of the invention, mammals, and specifically humans, suffering from brain stroke or spinal cord injury or of some other described condition, can be treated by locally (topically) administering to the patient an effective amount of active agents(s) in the presence of a pharmaceutically acceptable carrier or release matrix or diluent.

The active agent(s) is (are) included in the pharmaceutically acceptable carrier, release matrix or diluent in an amount sufficient to deliver to a patient a therapeutic amount of active agent(s), in vivo, in the absence of serious toxic effects. In general, local effect can be achieved by locally (topically) administering lower doses of active agent(s) than would be required if the agents were administered systemically. Typical dosages for local application for all of the above-identified conditions are those ranging from 0.001% to 100% by weight of the active composition.

Suitable vehicles or carriers or release matrices for local application are, e.g., lotions, suspensions, ointments, creams, gels, tinctures, sprays, powders or pastes.

Active agent(s) can be applied in a time release formulation also via patches or by (slow) release polymer matrices. The active compounds can be prepared with carriers or release matrices that will protect the compound against too rapid release, such as controlled release formulations, like microencapsulated delivery systems, or bioabsorbable fibers, fiber constructions, like theads, cords, bands, knitted or woven fabrics, meshes and films.

Fibers are typical bioabsorbable polymeric active agents releasing matrices, typically 1–300 $\mu$m in diameter and of different lengths. For example, the fibers can be very short (1–50 $\mu$m in length) acting as microparticles. They can also be short-fibers (typically with lengths between 50 $\mu$m–5 mm) or long-fibers, longer than 5 mm in length. The long and/or short fibers can be fabricated into different textile products, like non-woven felts and sheets and knitted or woven fabrics.

Suitable bioabsorbable polymers to be used in manufacturing of such formulations are mentioned, e.g., in U.S. Pat. No 4,968,317, U.S. Pat. No 5,618,563, FI Pat. No 98136, FI Pat. No 100217B, the entire disclosures of which are incorporated herein by way of this reference.

According to an advantageous embodiment of the invention, the active agent(s) and/or composition can be injected directly into injured or ischemic brain area (e.g. as a solution which also contains active agent(s) releasing microcapsules or nanocapsules).

The active agent(s) also can be incorporated into a bioabsorbable implant, like mesh or other fabric, or into a film (implant) releasing active agent(s), which implant can be located on the surface of the brain or into the brain tissue of the ischemic tissue area.

In addition to the other materials listed above for systemic administration, thickening agents, emollients, and stabilizers can be used to prepare topical compositions. Examples of thickening agents include petrolatum, beeswax, xanthan gum, or polyethylene glycol, emolients such as mineral oil, lanolin and its derivatives, or squalene.

E. Optional Components

Whether administered locally (topically) or systemically, the active agent(s) and/or active composition(s) can also be mixed with other active materials which do not impair the desired action, or with materials that supplement the desired action, such as other antibiotics, neuroprotective drug(s), anti-inflammatories, antivirals, or other agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyll parabens; antioxidants such as ascorbic acid or sodium bisulfite; chelating agents such as ethylenediaminetetraacetic acid; buffers such as acetates, citrates or phosphates and agents for the adjustment of tocicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

III. Modification of Tetracycline Derivatives

The tetracycline derivatives can be modified in order to enhance their usefulness as pharmaceutical compositions in treatment of brain stroke and/or spinal cord injuries. For example, it is well known in the art that various modifications of the active molecule, such as alteration of charge, can affect water and lipid solubility and thus alter the potential for blood-brain barrier or brain and/or spinal cord penetration. The vehicle, or carrier or release matrix can also be modified to enhance such penetration or to enhance the reservoir effect.

IV. Combination Therapy

According to an advantageous embodiment of the invention, the active agent(s) and/or active composition is used as a part of a combination therapy to achieve the optimal result to prevent and suppress the negative results of a brain stroke and/or spinal injury. For example, the active agent(s) and/or active composition can be administered during the ambulance ride to the hospital. This early administration can be combined, e.g., with the administration of a thrombolytic drug (like Activase, a recombinant tissue plasminogen activator, tPA, available from GENENTECH of California, USA). The administration of the active agent(s) and/or active composition can then be continued in combination with hospital procedures, like with neurointerventional procedures, when, e.g., a rheolytic or laser-based clot removal device is used for the treatment of the occlusive stroke. Such devices are, e.g., a pulsed-dye laser system of LATIS (available from Horsham in Pennsylvania, USA) and ANGIOJET rheolytic thrombectomy system of POSSIS MEDICAL (of Minneapolis, Minn., USA). After clot removal, the treated artery can be equipped with a stent to keep the treated artery open (see, e.g., MedPro Month VI[11–12]:274, 1996, the entire disclosure of which is incorporated herein by way of this reference). According to an advantageous embodiment of the invention, the stent can be coated with a polymer layer releasing active agent(s) into the wall of the artery and through it into the ischemic tissue. The stent can also be manufactured of a bioabsorbable polymer releasing active agent(s) and possible other active substances into the wall of the artery.

The active agent(s) and/or active composition can be administered also in combination with Retrograde Transvenous Neuroperfusion (RTN) (of NEUROPERFUSION, Ivine, Calif., USA) where oxygenated blood from the femoral artery in the leg is pumped back into the brain via the jugular vein. Ultimately, this blood reaches the ischemic tissue affected by the stroke, providing there oxygen and the active agent(s) and/or active composition.

V. Preventive (Prophylactic) Therapy

According to an advantageous embodiment of the invention, the active agent(s) and/or active composition is given to people with a risk of a stroke (e.g., to people who have suffered transient ischemic attacks) as preventive therapy. For example, a systemic administration can be made 1–3 times a day, or the active composition can be administered in a polymeric (optionally bioabsorbable) implant, which can be implanted into a soft tissue, like muscle tissue, or near a carotid artery, which implant releases slowly the active agent(s) into blood circulation to reduce the risk of a stroke for the patient.

The present invention is further described with reference to the following non-limiting examples.

EXAMPLE 1

Neuroprotections by Systemic Administration of Tetracycline Derivatives in Global Ischemia Adult male Mongolian gerbils (Meriones Unguiculatus, 60–65 g body weight) were received from Tumblebrook Farm (West Brookfield, Mass., USA). They were housed in standard temperature (22+1° C.) and light-controlled (light period 07:00–21:00 h) environment with ad libitum access to food and water. After a 10-day quarantine period, animals were acclimated to the vivarium facility for several days. Immediately prior to surgery, each subject was anesthetized with 5% halothane (70% $N_2O$/30% $O_2$). During surgery, halothane was lowered to 1–2%. A midline incision was made in the neck and surgical silk was loosely placed around isolated carotid arteries. Anesthesia was disconnected and atraumatic miniature aneurysm clips were attached to occlude both carotid arteries for 6 min. The body temperature was maintained at 36–37° C. during the surgery with a heating pad. All surgical procedures, including the verification of the absence of blood flow during the occlusion as well as restoration of flow after removal of the clips, were inspected under stereomicroscopic control. For operations, the carotic arteries were exposed and separated from surrounding tissue and the vagus nerve. The animals were treated with intraperitoneal injections of minocycline HCL, doxycycline HCL (both drugs from Sigma Chemical Co., St Louis, Mo., USA), diluted in $H_2O$, pH 6.5–7.0 or an equivalent volume (0.5 ml) of physiological saline. All the treatments and surgical procedures were approved by the local committee for the welfare of faboratory animals.

The treatment protocols are given in Table I.

TABLE I

Administration of minocycline and doxycycline in global brain ischemia: mg/kg i.p.

| -12 h | isch | 12 h | 24 h | 36 | 48 h | 60 h | 72 h | 84 | 96 h | 108 | 120 h | 132 h | 144 h |
|---|---|---|---|---|---|---|---|---|---|---|---|---|---|
| 45 | 90 | 90 | 90 | 45 | 45 | 45 | 45 | 45 | 45 | 45 | 45 | 45 | 45 |
| 20 | 40 | 40 | 40 | 20 | 20 | 20 | 20 | 20 | 20 | 20 | 20 | 20 | 20 |
| 10 | 20 | 20 | 20 | 10 | 10 | 10 | 10 | 10 | 10 | 10 | 10 | 10 | 10 |

TABLE I-continued

Administration of minocycline and doxycycline in global brain ischemia: mg/kg i.p.

| -12 h | isch | 12 h | 24 h | 36 | 48 h | 60 h | 72 h | 84 | 96 h | 108 | 120 h | 132 h | 144 h |
|---|---|---|---|---|---|---|---|---|---|---|---|---|---|
|  | 90* | 90 | 90 | 45 | 45 | 45 | 45 | 45 | 45 | 45 | 45 | 45 | 45 |
|  | 45* | 45 | 45 | 20 | 20 | 20 | 20 | 20 | 20 | 20 | 20 | 20 | 20 |
|  | 90* | — | — | — | — | — | — | — | — | — | — | — | — |

*Administered 30 min after ischemia. The number of the animals was 8 in each group.

The animals were deeply reanaesthetized with an overdose of pentobarbital (Mebunat$^R$ 60 mg/ml) and perfused intracardially with phosphate-buffered saline (pH 7.2) until the effluent was cleared of blood (2 minutes), followed by perfusion with 4% paraformaldehyde (300 ml in 0.1 M phosphate-buffered saline). The brain was removed and a 6-mm coronal slice containing the dorsal hippocampus was postfixed in the same fixative for another 4 hours. After rinsing in phosphate buffer the samples were cryoprotected for 48 hours in 20% sucrose solution and quickly fiozen in isopentane cooled to $-30°$ C. on dry ice. Ten-micron thick sections were taken through the dorsal hippocampus (2–4 mm posterior to Bregma) and mounted on gelatin-coated slides and stained with Cresyl Fast Violet. Under light microscopy (320× magnification), all normal appearing CA1 pyramidal neurons in a 350 $\mu$m length of the medial CA1 region were counted bilaterally and averaged. In animals that showed significant asymmetry in regards to the CA1 neuronal counts (>50% difference between hemispheres; about 10% of the animals), the hemisphere with the lower count (i.e., more severely affected) was included in the analysis.

The neuronal counts were consistently performed in a blind manner as to the identification of tetracycline derivative-treated gerbils. All the data are expressed as means±S.D. Statistical evaluation Was performed using Student's t-test (unpaired for comparison between different groups of gerbils).

Figure 2:
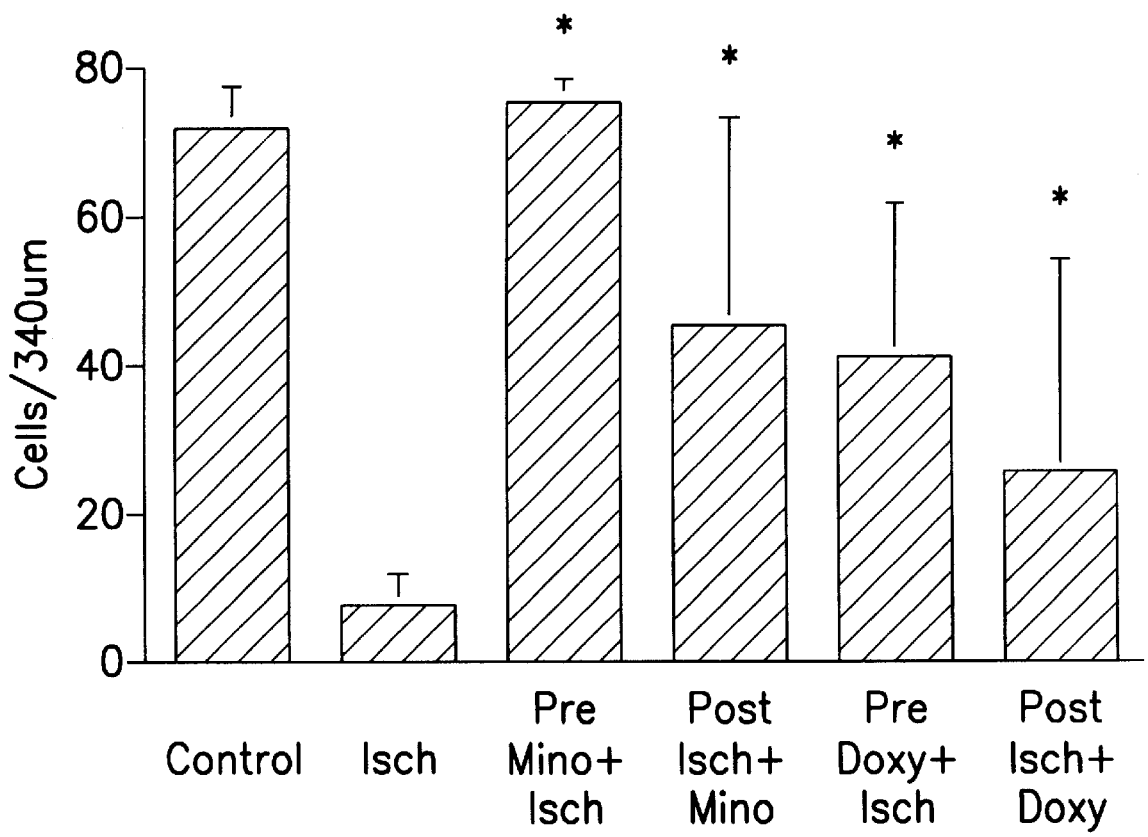
FIG. 2 describes the effect of pre- and post ischemic treatment (Co and Isch, respectively) with minocycline (mino) and doxycycline (doxy).

Effect of Systemic Minocycline and Doxycycline on Ischemic Neuronal Death in the CA1 Pyramidal Cell Layer FIG. 2 illustrates the effect of minicycline and doxycycline given at the highest dose, intraperitoneally, twice a day for 6 days beginning either 12 hours prior to or 30 min after ischemia The doses were as indicated in Table I. As indicated, minocycline treatment increased the neuronal survival from 10% to 100% and to 60% when the treatment was started 12 hours prior to or 30 min after the ischemia, respectively. Correspondingly, doxycycline increased the neuronal survival to 54.5% and 33.6% when the treatment was started 12 hour prior to or 30 min after the ischemia.

Table I illustrates the effect of systemic minocycline and doxycycline given at the lowest doses, intraperiotenally, twice a day for 6 days, beginning either 12 hours prior to or 30 min after ischemia. As indicated, minocycline increased the neuronal survivals from 10% to 50% and to 28% when the treatment was started 12 hours prior to or 30 min after the ischemia, respectively. Correspondingly, doxycycline increased the neuronal survival to 26% and 16% when the treatment was started 12 hours prior to or 30 min after ischemia, respectively. The gerbils treated with the tetracycline derivatives at any dose shown retained the same physical activity when compared to untreated ischemic gerbils, and appreared to have normal interest in food and water. Routine histological examination of kidney, liver or spleen did not demonstrate any abnormalities. There were no significant differences in the body temperature or blood gas values between different groups.

EXAMPLE 2

Neuroprotections by Local Administration of Active Agent (s) in Global Ischemia

Manufacturing of Active Agent(s) Releasing Meshes

Bioabsorbable polymer and the active agent (tetracycline, derivative or tetracycline and/or derivative mixture) were dissolved into an organic solvent in w/w ratio 100/8 (polymer/active agent). If the active agent did not dissolve into the organic sovent, it was dispersed as a fine powder (particle diameters <3$\mu$m) into the polymer solution. The concentration of polymer was 10% (w/w) in solution.

The polymer solution was heated to 50° C. and spun into a continuous fiber by pressing the solution through a conical spinning die (orifice diameter 1 mm) into a vacuum chamber (p<0.1 torr). In vacuum, the solvent evaporated and a continuous fiber was formed. The fiber was collected at the other end of a 1 m long vacuum chamber on a rotating cylinder. The speed of fiber spinning was 40 cm min$^{-1}$.

The fibers were drawn at elevated temperatures (RT→70° C.) to draw ratios $\lambda$2–6, to toughen the fibers.

The fibers were knitted into tricot fabric tube (with the stitch size of 1 mm with a knitting machine). The tube was cut open along its long axis so that long, 4 cm wide bioabsorbable polymer fiber fabrics (containing 8% (w/w) of tetracycline derivative(s)) were achieved. The fabrics were cut to mesh-samples of 40×40 mm. The meshes were immersed for 5 min into the saturated water solution of the same active agent, which was incorporated into the mesh, dried and packed into plastic bags and sterilized with $\gamma$-radiation.

Manufacturing of an Active Agent Releasing Hydrogel

Gelatin with an isoelectric point of 4.9 was isolated from bovine bone by the standard alkaline process. The weight-average molecular weight was 60,000 when measured by gel filtration chromatography relative to standard polyethylene glycol samples.

Gelatin in 10% aqueous solution was chemically crosslinked with glutaraldehyde at 25° C. to prepare hydrogels with different extents of crosslinking. In accordance with Y. Tabata el al., J. Cont. Rel., 31 (1994)189–199, the entire disclosure of which is incorporated herein by reference, an aqueous gelatin solution containing glutaraldehyde was cast in a Teflon mold (5×5 cm$^2$, 1.0 mm deep). Following the crosslinking reaction, which lasted for 12 hours at 25° C., the resulting hydrogels were immersed in 50 mM of glycine aqueous solution at 37° C., for 1 hour, to block residual aldehyde groups of glutaraldehyde, rinsed by distilled water, 100% ethanol, and autoclaved distilled water. These were freeze dried, followed by impregnation with an aqueous solution containing 100 mg minocycline, to obtain gelatin hydrogels that incorporated minocycline. Empty gelatin hydrogels were prepared similarly, except that they were prepared with an aqueous phosphate-buffered saline (PBS) solution without minocycline. The water content, defined by the weight percentage of water in the wet hydrogel, was determined from the hydrogel weight before and after swelling at 37° C. in PBS (pH 7.4). The water contents of the gelatin hydrogels used in the present study were 98% and 85%. All experimental processes were conducted under sterile conditions.

The sterile meshes and hydrogels were used as sustained release implants to release tetracycline derivative(s) into their surroundings when implanted on the brain surface in an animal (gerbile) model.

The ischemia was created according to Example 1. A sterile mesh sample (size 3×4 mm) was located on the brain surface 10 min after the ischemia, and the neuronal survival was studied after 72 h with the methods of Example 1.

Table II illustrated the studied polymers, active agents, solvents and the mean neuronal survival % (MNS %) of the corresponding animal groups when measured 72 hours after the implantation of the mesh.

of 1000 kg/cm$^2$. The mixture was momentarily heated from the solid to the molten state, after which it was cooled rapidly to RT. The resulting solid mixture in the form of a small cylinder was then removed and crushed. The crushed mixture was sieved and particles smaller than 50 μm in diameter were inserted into a flat film mold and pressed at 50° C. for two minutes to obtain a polymeric film (dimensions 1 mm×30 mm×30 mm) including 8% of active agents (M-PDLA(2)). The films were cut to a size 3×10 mm, dried, packed in Al-foil pouches, which were closed and γ-sterilized.

Male New Zealand White rabbits weighing 2 to 3 kg were used. All the rabbit procedures were approved by the local committee for the welfare of laboratory animals. The rabbits were housed in standard temperature (22+1° C.) and light-

TABLE II

The efficacy of bioabsorbable meshes, releasing active agent(s) in preventing of cell-death in the ischemic brain of gerbile

| Polymer | Active agent(s) | Solvent | MNS (%) |
|---|---|---|---|
| Poly-D,L-lactide 50/50 $M_w$ = 2000 (1) | Minocycline | Chloroform | 60 |
| Poly-D,L-lactide-co-glycolide 75/25 i.v. 0.6 (1) | Minocycline + Doxicycline (1:1) | Dichloromethane | 35 |
| Poly-D,L-lactide 50/50 $M_w$ = 20 000 (2) | Tetracycline + Minocycline (ratio 1:1) | Chloroform | 40 |
| Polyanhydride (3) | Minocycline | Chloroform | 65 |
| Polyanhydride (3) | CMT-3 (6) | Chloroform | 80 |
| Polyorthoester (4) | Doxicycline | Tetrahydrofuran | 40 |
| Tyrosine polycarbonate (5) | CMT-8 (7) | Methylene chloride | 55 |
| Gelatin | Minocycline | Water | 80 |

(1) Manufacturer: Boehringer Ingelheim, Germany
(2) Manufacturer: CCA Purac, Holland
(3) Synthesized according to U.S. Pat. No. 5,618,563, EXAMPLE 1
(4) Acetate Polyorthoester, ($M_w$ = 6000), synthesized according to S. F. Bernatchez et al., J. Biomed. Mater. Res., 28 (1994) 1037–1046, the entire disclosure of which is incorporated herein by reference.
(5) Poly(DTH carbonate) ($M_w$ = 200 000), synthetized according to S. I. Ertel and J. Kohn, J. Biomed. Mater. Res. 28 (1994) 919–930 and F. H. Silver et al., J. Long-Term Effects Med. Implants 1 (1992) 329–346, the entire disclosures of which are incorporated herein by reference.
(6) Synthesized according to L. M. Golub et al., Crit. Review Oral Biol. Med., 2 (1991) 297–322, the entire disclosure of which is incorporated herein by reference.
(7) Synthesized according to A. R. Amin et al., FEBS Letters 410 (1997) 259–264, the disclosure of which is incorporated herein by reference.
The number of animals was 8 in each group.
MNS % = Mean neuronal survival % measured 72 h after the ischemia.

In addition to the drug treated groups, a control group without ischemia and an ischemia group without any treatment was included.

EXAMPLE 3

Treatment of Spinal Cord Ischemia in Rabbits with Minocycline Releasing PDLA—Mesh and Film.

Manufacturing of Minocycline Releasing PDLA-Film with Melt Molding Technique

Poly-D,L-lactic acid (PDLA) 50/50, $M_w$=4000 (supplied by CCA Purac, Holland) powder and a mixture of doxicycline and 6demethy 1,6-deoxy, 4-dedimethylaminotetracycline (ratio 50/50 w/w) were mixed with each other in such a ratio that the mixture contained 8% of tetracycline derivative mixture. The polymer-active agent mixture was inserted into a small cylinder and heated at 50° C. for 1.5 min under a pressure controlled (light-period 07:00–21:00 h) environment with ad libitum access to food and water. After a 3-week quarantine period, the rabbits were operated upon. Each rabbit was anesthetized with 5% halothane (70% $N_2O$: 30 % $O_2$). During surgery, halothane was lowered to 1.5–2%. Rabbits had a snare ligature occluding device placed around the abdominal aorta just below the left renal artery. The end of the occluder was left accessible through the skin. The rabbits were allowed to recover for a minimum of 2 hours. To induce ischemia, the occluder was tightened and clamped. All rabbits were completely paraplegic within 2 minutes. The animals showed no evidence of discomfort, and the procedure appears to be painless, based on lack of previously measured changes in heart rate and blood pressure. At the end of a 30-min occlusion period, the device was unclamped and removed, and the skin closed. The rabbits received one of the minocycline treatments given in Table III.

TABLE III

Systemic and local administration of minocycline (mg/kg) in paraplegic rabbits

|   | −12 h | isch | 12 h | 24 h | 36 h | 48 h | 60 h | 72 h | 84 h | 96 h | →30 d |
|---|---|---|---|---|---|---|---|---|---|---|---|
| A | 60 | 60 | 60 | 60 | 45 | 45 | 45 | 45 | 45 | 45 | |
| B | | 60* | 60 | 60 | 45 | 45 | 45 | 45 | 45 | 45 | |
| C | | M-PDLA(1) + 60* | → | → | → | → | → | → | → | → | → |
| D | | M-PDLA(2) + 60* | → | → | → | → | → | → | → | → | → |
| E | | 60* | | | | | | | | | |

A, B, E: The numbers mg/kg of minocycline given intraperitoneally.
C: M-PDLA(1) = Poly-D,L-lactic acid mesh (3 mm × 10 mm) with 8% (w/w) of minocycline according to Example 2, was implanted to the ischemic spinal cord 30 min after ischemia.
D: M-PDLA(2) = Poly-D,L-lactic acid film (3 mm × 10 mm) with 8% (w/w) of minocycline, was implanted as M-PDLA(1).
*Administered 30 min after ischemia.

In addition to the groups A–E, a control group without ischemia and an ischemia group without any treatment was included. The number of the animals was 8 in each group.

In groups C and D the animals received an intraperitoneal injection of minocycline 30 min after ischemia. Subsequently, laminectomy of the lumbar and sacral vertbrae was performed under halothane anesthesia (1.5% in 70% $N_2O$:30% $O_2$), and a M-PDLA mesh or film was carefully placed to fully cover the dorsal surface of the spinal cord area from L2 segment to S2 segment The mesh or film was fixed with four drops of a tissue adhesive (Histoacryl, B. Braun Melsungen AG, Germany), the bone closed with President paste (light body, Cotene, Switzerland) and the skin closed with few knots. Thirty days after ischemia all the animals were reanesthetized with an overdose of pentobarbital (Mebunat, 60 mg/ml), perfused intracardially with phosphate-buffered saline (pH 7.2) until the effluent was cleared of blood (4 minutes), followed by perfusion with 4% paraformaldehyde (600 ml in 0.1 M phosphate-buffered saline). The spinal cord was removed and the slice containing the lumbar and sacral segments was postfixed in the same fixative for another 4 hours. After rinsing in phosphate buffer, the samples were cryoprotected for 48 hours in 20% sucrose solution and quickly frozen in the isopentane cooled to −30° C. on dry ice. Ten-micron thick cryosections were taken and mounted on gelatin-coated slides and immunostained with a monoclonal mouse SMI-32, an antibody to non-phosphorylated neurofilaments which serves as a marker for spinal motor neurons. Under light microscopy (320× magnification), the number of the surviving motor neurons was evaluated from standardized sections throughout the lumbar and sacral spinal cord, using MCID image analysis system. The neuronal counts were consistently performed in a blind manner as to the identification of minocycline-treated rabbits. All the data are expressed as means±S.D. Statistical evaluation was performed using Student's t-test (unpaired for comparison between different groups of rabbits).

The effect of systemic and topical minocycline treatment in the rabbit spinal cord ischemia after 20 days was as follows. Systemic minocycline treatment increased motor neuron survival from 10% to 75% when started 12 h prior to ischemia. The survival of the neurons was increased to 54% when administered 30 min after ischemia for the first time. One injection of 60 mg/kg minocycline 30 min after ischemia did not increase the motor neurons survival, but when M-PDLA mesh or film was inserted the survival was significantly increased to 48% and 35%, respectively, roughly corresponding to the efficiency of systemic minicycline administration in this model. The study also demonstrated a long-term survival of the motor neurons by minocycline treatment after ischemia. The physical activity and motor functions were better in chronically minocycline-treated animals compared to untreated rabbits (not shown).

The treated rabbits had a normal interest in food and water. Routine histological examination of kidney, liver or spleen did not demonstrate any abnormalities. There were no significant differences in the body temperature or blood gas values between different groups.

EXAMPLE 4

Treatment of Focal Brain Ischemia in the Rat: Beneficial Effect of Active Agent(s) Releasing Microparticles.

Manufacturing of Minocycline Releasing PDLGA-Microparticles with W/O Emulsion Technique Poly (D,L-lactide-co-glycolide) (PDLGA) (75/25), (i.v. 0.8, manufacturer Boehringer Ingelheim, Germany) was dissolved in dichloromethane to a concentration of 0.5 g/ml. Minocycline was dispersed and dissolved in water (concentration 1 g/ml). One part of minocycline solution and 5 parts of polymer solution were vigorously homogenized with an ultrasound mixer to make a w/o emulsion. The emulsion was cooled to room temperature and poured through a thin nozzle into 800 ml of a 0.1% polyvinyl alcohol aqueous solution under stirring, and the resulting mixture was stirred for a few minutes to make a w/o/w emulsion. To evaporate the dichloromethane, the w/o/w emulsion was further stirred with a propeller mixer for 3 h. After removing particles larger than 100 μm by sieving, the resulting microparticles were collected by centrifuging for 10 min at 2000 rpm, rinsed with water three times and then freeze dried to yield a powder. The microparticles (M-PDLGA(1)) were packed in plastic bags and γ-sterilized.

Manufacturing of Minocycline Releasing PDLGA-Microparticles with W/O/W Emulsion Technique Poly (D,L-lactide-co-glycolide) (PDLGA) (75/25), (i.v. 0.8, manufacturer Boehringer Ingelheim, Germany) was dissolved in dichloromethane to a concentration of 0.5 g/ml. Minocycline was dispersed and dissolved in water (concentration 1 g/ml). One part of minocycline solution and S parts of polymer solution were vigorously homogenized with an ultrasound mixer to make a w/o emulsion. The emulsion was cooled to room temperature and poured through a thin nozzle into 800 ml of a 0.1% polyvinyl alcohol aqueous solution under stirring, and the resulting mixture was stirred for a few minutes to make a w/o/w emulsion. To evaporate the dichloromethane, the w/o/w emulsion was further stirred with a propeller mixer for 3 h. After removing particles larger than 100 μm by sieving, the resulting microparticles were collected by centrifuging for 10 min at 2000 rpm, rinsed with water three times and then freeze dried to yield a powder (M-PDLGA(2)).

Manufacturing of Minocycline Releasing Microparticles (+Nanoparticles) with Spray-Drying Minocycline and poly-DL-lactic co-glycolide (PLGA 50/50, intrinsic viscosity 2 dl/g; manufacturer CCA Purac, Holland) were dissolved into methylene chloride so that the minocycline/PLGA ratio (w/w) was 8/100 and their total concentration in solution was 5%

The solution was spray-dried by atomizing it with a high pressure nozzle injection into a vacuum chamber. The resultant microcapsules were dried in high vacuum at room temperature for several days, and a fraction of 0.5–60 μm diameter nano- and microcapsules (M-PDLGA(3) )were collected with sieving.

Animal Study

Focal cerebral ischemia was produced by intraluminal nylon thread introduction. Male Wistar rats (250–300 g) were anesthetized with 5% halothane (70% $N_2O$ and 30% $O_2$) and during the operation halothane concentration was reduced to 0.5%. The rectal temperature of the animal was maintained between 37.0–37.5° C. with a heating pad. For recording of physiological parameters, a polyethylene catheter was inserted into femoral artery. The left common artery was exposed, and the external carotid artery was ligated. A 0.25 mm nylon thread was inserted into the internal carotid artery up to the anterior cerebral artery. Following 90 min of ischemia, restoration of the MCA blood flow was performed by removing the suture. Twenty-six days after ischemia, the animals were anesthetized with an overdose of pentobarbital (Mebunat$^R$; 60 mg/ml, i.p.) and decapitated. The brains were rapidly removed from the skull and frozen on dry ice. Coronal sections (40 μm) were cut on SuperFrost slides (Menzel-Gläzer, Braunschweig, Germany). Sections were stained for 20 min with a solution containing 1.2 mM nitro blue tetrazolium, 0.1 M Na-succinate in 0.1 M Na-phosphate buffer, pH 7.6 at 37° C. After rinsing and coverslipping the infarcted area in the cortex was determined according to the indirect method described in Swanson R A, Morton M T, Tsao-Wu G, Savolas R A, Davidson C and Sharp F R (1990) J. Cereb. Blood Flow Metab. 10:290–299, the entire disclosure of which is incorporated herein by this reference. Areas of surviving gray matter with optical densities above the threshold value (taken from the corpus callosum) were automatically recognized and measured separately for each hemisphere The difference of the size of an intact area in the contralateral hemisphere and the respective residual area in the ipsilateral hemisphere was taken as the infarcted area. Total infarct volume was calculated by multiplying the infarct area by the distance between sections and by summing together with infarct volumes. The rats were treated according to Table IV.

two locations in the cortex. The bone wholes were covered with President paste and Histoacryl (see Example 2) and the skin closed.

Effect of systemic and M-PLGA microparticles on focal brain ischemia was the following one. When the systemic minocycline treatment was started 12 hour prior to brain ischemia and continued for four days, the cortical infarction area was reduced at 26 days by 65% compared to untreated ischemia animals. The 4-day minocycline treatment that was started 30 min after ischemia decreased the cortical infarction by 26%. A single intraperioteal minocycline injection alone 30 min after ischemia did not provide protection against ischemia, whereas in combination with microparticle treatments (M-PDLGA (1), (2) and (3)) protections of 22%, 18% and 30% were achieved, respectively. The treated rats had physical activity comparable to the nontreated rats, and showed normal interest in food and water. Routine histological examination of kidney, liver or spleen did not demonstrate any abnormalities. There were no significant differences in the body temperature, blood pressure or blood gas values between different groups.

EXAMPLE 5

Combination Treatment of Focal Brain Ischemia with M-PDLGA(3) and Tissue Plasminogen Activator (tPA)

A fibrin-rich thrombotic focal cerebral ischemic model of the rat was used to test the effect of combined treatment with tPA and minocycline. See Zhang Z, Zhang R L, Jiang Q, Raman S B K, Cantwell L and Chopp M (1997). J. Cereb. Blood Flow Metab. 17:123–135, the entire disclosure of which is incorporated herein by way of this reference. Male Wistar rats, weighing 300–450 g were anesthetized as described in Example 3. The right and left common carotic arteries, the right external carotic artery, and the internal carotid artery were isolated via a midline incision. A 5-0 silk suture was tied loosely at the origin of the ECA and ligated at the distal end of the ECA. The right CCA and ICA were temporarily clamped using a curved microvascular clip. A modified PE-50 catheter (0.3 mm O.D.), filled with bovine α-thrombin (10 NIH U/μl), was attached to a 100 μl Hamilton syringer and introduced into the ECA lumen through a small puncture. The suture around the origin of the ECA was tightened around the intraluminal catheter to prevent bleeding and the microvascular clip was removed. A 15-mm

TABLE IV

Systemic and local administration of minocycline (mg/kg) in ischemic rats

|   | −12 h | isch | 12 h | 24 h | 36 h | 48 h | 60 h | 72 h | 84 h | 96 h | →26 d |
|---|---|---|---|---|---|---|---|---|---|---|---|
| A | 45 | 45 | 45 | 45 | 45 | 20 | 20 | 20 | 20 | 20 | |
| B | | 45* | 45 | 45 | 45 | 20 | 20 | 20 | 20 | 20 | |
| C | | M-PDLGA(1) + 45* | → | → | → | → | → | → | → | → | → |
| D | | M-PDLGA(2) + 45* | → | → | → | → | → | → | → | → | → |
| E | | M-PDLGA(3) + 45* | → | → | → | → | → | → | → | → | → |
| F | | +45* | | | | | | | | | |

The numbers indicate mg/kg of minocycline given intraperitoneally.
C, D, E: M-PDLGA(1), (2) and (3) = poly(D,L-lactic-co-glycolide) microparticles and nanoparticles with minocycline (10 μg/kg) injected in the volume of 3 × 1.5 μl in the ischemic tissue 30 min after ischemia.
In addition, a group of untreated ischemic rats was included to the experiment.
*Administered 30 min after ischemia.

The number of the animals was 8 in each group.

In groups C, D and E, the animals received an intraperitoneal injection of minocycline 30 min after ischemia. Subsequently, two 2-mm craniotomies were made to the skull overlaying the ischemic cerebral cortex. One injection of 1.5 μl M-PDLGA (1) (2) or (3) composition was made over the period of 3 min in the lateral striatum and in length of catheter was gently advanced from the ECA into the lumen of the ICA. At this point, the intraluminal catheter was 2–3 mm from the origin of the MCA. Then, 10 μl of arterial blood was withdrawn into the catheter and retained for 10 min to form a clot. At 10 min after withdrawn of blood, the right and left CCA were temporalily clipped to reduce CBF and the clot in the catheter was injected into the ICA along with 80 U of α-thrombin. The clip on the left CCA was removed 5 min after injection and the catheter was withdrawn from the right ECA 10 min after injection. The right ECA was ligated. The clip on the right CCA was released 15 min after injection. The duration of the entire surgical procedure was about 45 min. The neurological examinations were performed at 2, 24 and 168 h after injection of thrombin. The neurologic findings were scored on a five-point scale: no neurologic deficit, 0; right Homer's sydrome, 1; failure to extend left forepaw fully, 2; turning to left, 3; circling to left, 4.

The treatment protocol is given in Table V.

TABLE V

Combined treatment of focal brain ischemia in rats

|   | isch + 30 min | 12 h | 24 h | 36 h | 48 h | 60 h | 72 h | 84 h | 96 h |
|---|---|---|---|---|---|---|---|---|---|
| A | 45 | 20 | 20 | 20 | 20 | 20 | 20 | 20 | |
| B | 45 + rt-PA | 20 | 20 | 20 | 20 | 20 | 20 | 20 | |
| C | rt-PA | | | | | | | | |

The numbers indicate mg/kg of minocycline given intraperitoneally.
A: M-PDLGA(3) of Example 4, was administered 30 min after ischemia for the first time.
C: rt-PA (Genentech, Inc., South San Francisco, CA) was administered 90 min after ischemia at a dose of 10 mg/kg body wt as a 10% i.v. bolus and the remainder continuously infused (i.v.) over a 30-min interval.
B: Combined treatment Animals were sacrificed 96 hours after ischemia
Also, an ischemia group without any treatment was included.

The number of the animals was 8 in each group.

The size of the infarcted area was quantified as desribed in Example 3. In this experiment post-ischemic treatment with minocycline-releasing M-PDLGA(3) decreased the infarct size by 29% (statistically significant), the rt-PA treatment by 47% (statistically significant), and the combined M-PDLGA(3)+rt-PA treatment by 61%, indicating a synergistic effect of these compounds on the outcome after focal brain ischemia.

EXAMPLE 6

Treatment of Global Brain Ischemia with Chemically Modified Tetracyclines.

Global ischemia in gerbils was produced as described in Example 1. CMT-3 derivative was used according to the treatment protocol of Table VI.

mg/mil suspension by forced feeding twice a day at the dose of 60 mg/kg, starting at 12 h prior to ischemia. At 36 h postischemia, the dose was reduced to 30 mg/kg and the treatment was continued for 6 days. A control group was forced-fed with phosphate-buffered saline, which was used as a vehicle. Eight gerbils were included in both groups. The ischemic damage was determined as described in Example 1. Oral minocycline treatement increased the neuronal survival from 10% to 55%. No significant changes were detected in blood gas values, blood pressure, or body temperature. Routine histological examination of kidney, liver or spleen did not demonstrate any abnormalities.

We claim:

1. A method for treating or suppressing neural injury conditions, comprising the steps of:

(1) preparing an effective amount of active composition comprising: (a) an active agent selected from the group consisting of one or more tetracycline derivatives, and mixtures of tetracycline and one or more tetracycline derivatives, and (b) a pharmaceutically acceptable release system comprising microcapsules or nano capsules, and (2) applying the active composition to a patient systemically to treat or suppress a neural injury condition.

2. The method of claim 1, wherein the condition to be treated is brain stroke.

TABLE VI

Administration of CMT-3 tetracycline derivative in global brain ischemia; mg/kg i.p.

| −12 h | isch | 12 h | 24 h | 36 h | 48 h | 60 h | 72 h | 84 | 96 h | 108 | 120 h | 132 h | 144 h |
|---|---|---|---|---|---|---|---|---|---|---|---|---|---|
| 10 | 10 | 10 | 10 | 5 | 5 | 5 | 5 | 5 | 5 | 5 | 5 | 5 | 5 |
|  | 10* | 10 | 10 | 5 | 5 | 5 | 5 | 5 | 5 | 5 | 5 | 5 | 5 |

*Administered 30 min after ischemia. A control and an ischemia group without any treatment were also included. The number of the animals was 8 in each group.

The ischemic damage was determined as described in Example 1. When the CMT-3 treatment was started 12 hours prior to ischemia 100% protection was achieved. The post-ischemia treatment rsulted in 66% protection, comparable to that with minocycline or slightly better. No signs of side effects or toxicity were found in these animals.

EXAMPLE 7

Treatment of Global Brain Ischemia with Oral Minocycline Treatment

Global ischemia in gerbils was produced as described in Example 1, above. Minocycline was given orally in a 10

3. The method of claim 1, wherein the condition to be treated is spinal cord injury.

4. The method of claim 1, wherein the active composition is applied to the patient orally.

5. The method of claim 1, wherein the active composition is applied to the patient intravenously or intra-arterially.

6. The method of claim 1, wherein the active composition is applied to the patient intramuscularly.

7. The method of claim 1, wherein the active composition is applied to the patient through the peritoneum.

* * * * *

UNITED STATES PATENT AND TRADEMARK OFFICE
CERTIFICATE OF CORRECTION

PATENT NO. : 6,277,393 B1
DATED : August 21, 2001
INVENTOR(S) : Juha Yrjanheikki et al.

Page 1 of 1

It is certified that error appears in the above-identified patent and that said Letters Patent is hereby corrected as shown below:

Title page,
OTHER PUBLICATIONS, change "intercrnial" to -- intercranial --.

Column 1,
Line 44, change "ischemia A" to -- ischemia A --.

Column 8,
Line 55, change "faboratory" to -- laboratory --.

Column 9,
Line 21, change "fiozen" to -- frozen --.
Line 36, change "Was" to -- was --.

Column 14,
Line 67, change "5%" to -- 5%(w/v) --.

Column 15,
Line 35, change "hemisphere The" to -- hemisphere. The --.

Column 17,
Line 7, change "Homer's" to -- Horner's --.

Signed and Sealed this

Twenty-first Day of May, 2002

Attest:

*Attesting Officer*

JAMES E. ROGAN
*Director of the United States Patent and Trademark Office*